(12) United States Patent
Lee et al.

(10) Patent No.: US 12,104,192 B2
(45) Date of Patent: Oct. 1, 2024

(54) METHOD OF PREPARING PRIMARY AMINES FROM AMINO ACIDS USING ENZYMATIC CONVERSION

(71) Applicant: KOREA ADVANCED INSTITUTE OF SCIENCE AND TECHNOLOGY, Daejeon (KR)

(72) Inventors: Sang Yup Lee, Daejeon (KR); Dong In Kim, Daejeon (KR); Tong Un Chae, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 138 days.

(21) Appl. No.: 17/194,222

(22) Filed: Mar. 6, 2021

(65) Prior Publication Data

US 2021/0317486 A1  Oct. 14, 2021

(30) Foreign Application Priority Data

Apr. 8, 2020 (KR) ................. 10-2020-0042756

(51) Int. Cl.
| | | |
|---|---|---|
| C12N 9/88 | (2006.01) | |
| C12N 1/21 | (2006.01) | |
| C12P 13/00 | (2006.01) | |
| C12P 13/06 | (2006.01) | |
| C12P 13/08 | (2006.01) | |

(52) U.S. Cl.
CPC ............... *C12P 13/08* (2013.01); *C12N 9/88* (2013.01); *C12P 13/001* (2013.01); *C12P 13/06* (2013.01); *C12Y 401/01014* (2013.01)

(58) Field of Classification Search
None
See application file for complete search history.

(56) References Cited

U.S. PATENT DOCUMENTS

2007/0092957 A1   4/2007  Donaldson et al.

FOREIGN PATENT DOCUMENTS

| CN | 102336672 B | * | 6/2014 | |
|---|---|---|---|---|
| CN | 104919050 A | | 9/2015 | |
| CN | 106636047 A | * | 5/2017 | ............... C12N 9/88 |
| CN | 112852695 A | | 5/2021 | |
| EP | 2578559 A1 | * | 4/2013 | ........... C07C 291/04 |

OTHER PUBLICATIONS

Kim et al., Microbial production of multiple short-chain primary amines via retrobiosynthesis, Nature Comm. 12, Jan. 2021, 173. (Year: 2021).*
GenBank, Accession No. AY116644.1, 2003, www.ncbi.nlm.nih.gov. (Year: 2003).*
Bast et al., Uber eine Valin-Carboxylyase aus Bacillus sphaericus, Arch. Mikrobiol. 79, 1971, 12-24. (Year: 1971).*
"Gene Synthesis," Genscript, Jul. 21, 2019, website www.genscript.com/gene_synthesis.html, Internet Archive Way Back Machine, retrieved from webpage web.archive.org/web/20190721113005/ https://www.genscript.com/gene_synthesis.html?src=service, accessed on Aug. 1, 2023. (Year: 2019).*
Garg et al., Molecular characterization and analysis of the biosynthetic gene cluster for the azoxy antibiotic valanimycin, Mol. Microbiol. 2, 2002, 505-17. (Year: 2002).*
Rizhsky et al. (Integrating metabolomics and transcriptomics data to discover a biocatalyst that can generate the amine precursors for alkamide biosynthesis, Plant J. 8, 2016, 775-93. (Year: 2016).*
"GenBank: AAN10242.1_valine decarboxylase [Streptomyces viridifaciens]", Jul. 24, 2016.
Garg, R.P., et al., "Molecular characterization and analysis of the biosynthetic gene cluster for the azoxy antibiotic valanimycin", Molecular Microbiology, 2002, pp. 505-517, vol. 2, Publisher: 2002 Blackwell Publishing Ltd.
Anderhuber, N., et al., "High-level biosynthesis of norleucine in *E. coli* for the economic labeling of proteins", Journal of Biotechnology, 2016, pp. 100-111, vol. 235, Publisher: Elsevier; http://dx.doi.org/10.1016/j.jbiotec.2016.04.033.
Chen, C., et al., "Metabolic engineering of Corynebacterium glutamicum ATCC13869 for L-valine production", Metabolic Engineering, 2015, pp. 66-75, vol. 29, Publisher: Elsevier.
Lee, P.C., et al., "Batch and continuous cultivation of Anaerobiospirillum succiniciproducens for the production of succinic acid from whey", Appl Microbiol Biotechnol, 2000, pp. 23-27, vol. 54, Publisher: Springer-Verlag.
Lee, P.C., et al., "Succinic Acid Production with Reduced By-Product Formation in the Fermentation of Anaerobiospirillum succiniciproducens Using Glycerol as a Carbon Source", Biotechnol and Bioeng, 2001, pp. 41-48, vol. 72, No. 1, Publisher: John Wiley & Sons, Inc.
Lee, P.C., et al., "Isolation and characterization of a new succinic acid-producing bacterium, Mannheimia succiniciproducens MBEL55E, from bovine rumen", Appl Microbiol Biotechnol, 2002, pp. 663-668, vol. 58.
Lee, K.H., et al., "Systems metabolic engineering of *Escherichia coli* for L-theronine production", Molecular Systems Biology, 2007, Page(s) doi:10.1038/msb4100196, vol. 3, No. 149, Publisher: EMBO and Nature Publishing Group.
Lee, P.C., et al., "Biological conversion of wood hydrolysate to succinic acid by Anaerobiospirillum succiniciproducens", Biotechnology Letters, 2003, pp. 111-114, vol. 25, Publisher: Kluwer Academic Publishers.
Lee, P.C., et al., "Batch and continuous cultures of Mannheimia succiniciproducens MBEL55E for the production of succinic acid from whey and corn steep liquor", Bioprocess Biosyst Eng, 2003, pp. 63-67, vol. 26.

(Continued)

*Primary Examiner* — Todd M Epstein
(74) *Attorney, Agent, or Firm* — HULTQUIST, PLLC; Steven J. Hultquist

(57) ABSTRACT

Disclosed is a method of preparing primary amines. More particularly, disclosed are a mutant microorganism transformed with a gene encoding a valine decarboxylase and a method of preparing primary amines from amino acids using the mutant microorganism. The method has an effect of synthesizing, in an environmentally friendly manner, primary amines as precursors for pharmaceuticals and agricultural chemicals using microorganisms, as an alternative to conventional chemical synthesis methods.

3 Claims, 11 Drawing Sheets

Specification includes a Sequence Listing.

(56) References Cited

OTHER PUBLICATIONS

Liu, S.P., et al., "Heterologous pathway for the production of L-phenylglycine from glucode by *E. coli*", Journal of Biotechnology, 2014, pp. 91-97, vol. 186, Publisher: Elsevier.

Park, J.H., et al., "Metabolic engineering of *Escherichia coli* for the production of L-valine based on transcriptone analysis and in silico gene knockout simulation", Proc. Natl. Adac. Sci. USA, 2007, pp. 7797-7802, vol. 104, No. 19.

Park, H.J., et al., "Fermentative production of branched chain amino acids: a focus on metabolic engineering", Appl Microbiol Biotechnol, 2010, pp. 491-506, vol. 85, Publisher: Springer.

Park, J.H., et al., "Rational Design of *Escherichia coli* for L-Isoleucine Production", ACS Synthetic Biology, 2012, pp. 532-540, vol. 1, Publisher: ACS Publications.

Qingeng, H., et al., "Metabolic engineering of Corynebacterium glutamicum to enhance L-leucine production", African Journal of Biotechnology, 2017, pp. 1048-1060, vol. 16, No. 18.

Sycheva, E.V., et al., "Overproduction of Noncanonical Amino Acids by *Escherichia coli* Cells", Microbiology, 2007, pp. 712-718, vol. 76, No. 6.

Vogt, M., et al., "Pushing product formation to its limit: Metabolic engineering of Corynebacterium glutamicum for L-leucine overproduction", Metabolic Engineering, 2014, pp. 40-52, vol. 22, Publisher: Elsevier.

Yin, L., et al., "Co-expression of feedback-resistant threonine dehydratase and acetohydroxy acid synthase increase L-isoleucine production in Corynebacterium glutamicum", Metabolic Engineering, 2012, pp. 542-550, vol. 14, Publisher: Elsevier.

Zhang, X., et al., "Production of L-alanine by metabolically engineered *Escherichia coli*", Applied Genetics and Molecular Biotechnology, 2007, pp. 355-366, vol. 77, Publisher: Springer.

Zhang, K., et al., "Expanding metabolism for total biosynthesis of the nonnatural amino acid L-homoalanine", Proc. Natl. Acad. Sci. USA, 2010, pp. 6234-6239, vol. 107, No. 14.

Office Action Issued in Chinese Patent Application No. 202110363391.3 dated Jul. 19, 2023.

English Translation of Office Action Issued in Chinese Patent Application No. 202110363391.3 dated Jul. 19, 2023.

Search Report Issued in Chinese Patent Application No. 202110363391.3 dated Jul. 18, 2023.

* cited by examiner

METHOD OF PREPARING PRIMARY AMINES FROM AMINO ACIDS USING ENZYMATIC CONVERSION

CROSS-REFERENCE TO RELATED APPLICATION

The priority under 35 USC § 119 of Korean Patent Application 10-2020-0042756 filed Apr. 8, 2020 is hereby claimed. The disclosure of Korean Patent Application 10-2020-0042756 is hereby incorporated herein by reference, in its entirety, for all purposes.

REFERENCE TO SEQUENCE LISTING SUBMITTED VIA EFS-WEB

This application includes an electronically submitted sequence listing in .txt format. The .txt file contains a sequence listing entitled "556_SeqListing_ST25.txt" created on Mar. 6, 2021 and is 13,931 bytes in size. The sequence listing contained in this .txt file is part of the specification and is hereby incorporated by reference herein in its entirety.

BACKGROUND OF THE INVENTION

Field of the Invention

The present invention relates to a method of preparing primary amines from amino acids using enzymatic conversion. More particularly, the present invention relates to a mutant microorganism transformed with a gene encoding a valine decarboxylase and a method of preparing primary amines from amino acids using the mutant microorganism.

Description of the Related Art

Recently, a great deal of attention has been focused on sustainable manufacture of various value-added chemical products using microorganisms due to oil depletion and environmental problems. Among these value-added compounds, production of primary amines used as precursors for pharmaceuticals and agricultural chemicals using microorganisms is also being researched. However, there are no cases of successful production of a wide variety of primary amines using mutant microorganisms to date.

"Primary amine" refers to an amine formed by substituting one hydrogen atom of ammonia with an alkyl group or an aryl group, and is represented by the general formula $RNH_2$. Mutant microorganisms that produce amino acids that are precursors of primary amines using conventional metabolic engineering methods have not been reported to date. Representative examples include known mutant microorganisms that produce L-alanine, 2-aminobutyrate, L-norvaline, L-valine, L-norleucine, L-leucine, L-isoleucine and L-2-phenylglycine, which are precursor amino acids of primary amines such as ethylamine, propylamine, butylamine, isobutylamine, amylamine, isoamylamine, 2-methylamine and benzylamine.

In the case of mutant microorganisms that produce L-alanine and mutant microorganisms that produce 2-aminobutyrate, studies have been conducted on production using mutant microorganisms based on *Escherichia coli* (Zhang et al., *Appl. Microbiol. Biotechnol.* 77:355-366 2007; Zhang et al., *Proc. Natl. Acad. Sci. USA.* 107:6234-6239, 2010). L-norvaline and L-norleucine have been overproduced using *Escherichia coli* having engineered metabolic circuits (Sycheva et al., *Microbiology* 76:712-718, 2007; Anderhuber et al., *J. Biotechnol.* 235:100-111, 2016). L-valine, L-leucine and L-isoleucine, which are the branched-chain amino acids constituting proteins, were produced using the metabolic circuits of *Escherichia coli* and *Corynebacterium* strains (Park and Lee., Appl. *Microbiol. Biotechnol.* 85:491-506, 2010). In addition, L-2-phenylglycine has also been produced using mutant microorganisms based on *Escherichia coli* (Liu et al., *J. Biotechnol.* 186:91-97, 2014).

However, mutant microorganisms that directly produce primary amines using amino acids have not yet been reported.

Accordingly, as a result of extensive efforts to develop a method of preparing primary amines using microorganisms, the present inventors have discovered a decarboxylating enzyme that converts various kinds of amino acids as substrates into primary amines. The present inventors found that primary amines can be prepared in vitro as well as in vivo, that is, from various kinds of amino acids using mutant microorganisms transformed with the enzyme or the gene encoding the enzyme. Based on this finding, the present invention has been completed.

SUMMARY OF THE INVENTION

Therefore, the present invention has been made in view of the above problems, and it is one object of the present invention to provide a mutant microorganism capable of producing primary amines from amino acids.

It is another object of the present invention to provide a method of preparing primary amines using the mutant microorganism capable of producing primary amines from amino acids.

It is another object of the present invention to provide a method of preparing primary amines using enzymatic reaction.

In accordance with one aspect of the present invention, the above and other objects can be accomplished by the provision of a mutant microorganism capable of producing a primary amine from an amino acid, the mutant microorganism introduced with a gene encoding valine decarboxylase.

In accordance with another aspect of the present invention, there is provided a method of preparing a primary amine including (a) culturing the mutant microorganism to produce a primary amine, and (b) collecting the produced primary amine.

In accordance with another aspect of the present invention, there is provided a method of preparing a primary amine including (a) reacting a valine decarboxylase with an amino acid to produce a primary amine, and (b) collecting the produced primary amine.

Effects of the Invention

The present invention has an effect of synthesizing, in an environmentally friendly manner, primary amines as precursors for pharmaceuticals and agricultural chemicals using microorganisms, instead of conventional chemical synthesis methods.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Unless defined otherwise, all technical and scientific terms used herein have the same meanings as appreciated by those skilled in the field to which the present invention pertains. In general, the nomenclature used herein is well-known in the art and is ordinarily used.

The present invention first identified that a valine decarboxylase derived from *Streptomyces viridifaciens* has activity of converting various amino acids to primary amines through decarboxylation. In addition, a mutant microorganism transformed with a gene encoding the valine decarboxylase was produced, and the mutant microorganism was found to have the ability to convert amino acids into primary amines.

Accordingly, in one aspect, the present invention is directed to a mutant microorganism capable of producing a primary amine from an amino acid, in which a gene encoding a valine decarboxylase is introduced into the mutant microorganism.

According to the present invention, it was identified that the valine decarboxylase produces the corresponding primary amines using various amino acids as substrates, in addition to L-valine, which is a natural amino acid substrate, and a system that is capable of producing primary amines from amino acids using an enzyme was established based thereon.

Figure 1:
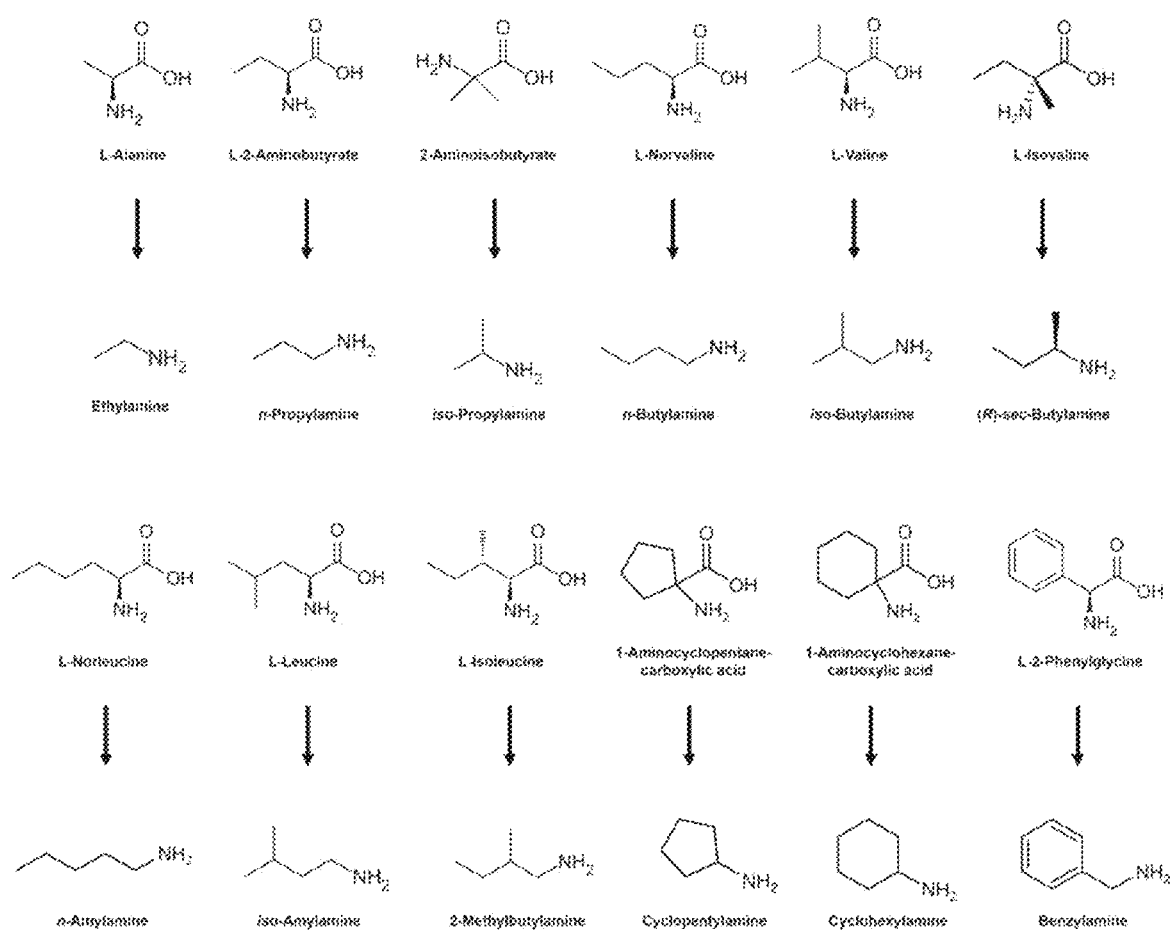
FIG. 1 shows a pathway for converting various amino acids into primary amines using valine carboxylase.

According to one embodiment of the present invention, the mutant microorganism produces ethylamine, propylamine, isopropylamine, butylamine, isobutylamine, (R)-sec-butylamine, amylamine, isoamylamine, 2-methylbutylamine, cyclopentylamine, cyclohexylamine and benzylamine using several amino acids as substrates (FIG. 1).

As used herein, the term "valine decarboxylase" refers to an enzyme encoded by a vlmD gene derived from *Streptomyces viridifaciens* and any enzyme having a homology with the enzyme.

In the present invention, the valine decarboxylase has the amino acid sequence represented by SEQ ID NO: 1 or has an amino acid sequence having homology of 90% or more with SEQ ID NO: 1, and has an activity of converting amino acids into primary amines.

According to the present invention, the gene encoding valine decarboxylase comprises the nucleotide sequence of SEQ ID NO: 2 or SEQ ID NO: 3 or a nucleotide sequence having homology of 90% or more with SEQ ID NO: 2 or SEQ ID NO: 3.

In one aspect, the present invention is directed to a method of preparing various primary amines including ethylamine, propylamine, isopropylamine, butylamine, isobutylamine, (R)-sec-butylamine, amylamine, isoamylamine, 2-methylbutylamine, cyclopentylamine, cyclohexylamine, and benzylamine from amino acids using a valine decarboxylase.

According to the present invention, it is revealed that the enzyme valine decarboxylase accepts various amino acids as substrates, in addition to L-valine, which is a natural amino acid substrate, and converts the same to the corresponding primary amines, and a system capable of producing various primary amines from amino acids using the enzyme is established based thereon (FIG. 1).

In the present invention, the enzyme that converts the amino acid into the primary amine may be a valine decarboxylase derived from *Streptomyces viridifaciens*, but any enzyme may be used without any limitation so long as it is expressed in host cells into which it is introduced and exhibits identical enzyme activity.

As used herein, the term "valine decarboxylase" refers to an enzyme encoded by a vlmD gene derived from *Streptomyces viridifaciens* and any enzyme having a homology with the enzyme.

According to the present invention, the primary amine is any chemical substance having the characteristics of an amine formed by substituting one hydrogen atom of ammonia with an alkyl group or an aryl group, and representative primary amines thereof include ethylamine, propylamine, isopropylamine, butylamine, isobutyl amine, (R)-sec-butylamine, amylamine, isoamylamine, 2-methylbutylamine, cyclopentylamine, cyclohexylamine, benzylamine, and the like.

Thus, the primary amine is selected from the group consisting of ethylamine, propylamine, isopropylamine, butylamine, isobutylamine, (R)-sec-butylamine, amylamine, isoamylamine, 2-methylbutylamine, cyclopentylamine, cyclohexylamine and benzylamine, but is not limited thereto.

In the present invention, the amino acid is any chemical substance characterized by having both an amine and a carboxylic acid functional group.

Representative amino acids are selected from the group consisting of L-alanine, L-2-aminobutyrate, 2-aminoisobutyrate, L-norvaline, L-valine, L-isovaline, L-norleucine, L-leucine, L-isoleucine, 1-aminocyclopentanecarboxylic acid, 1-aminocyclohexanecarboxylic acid, and L-2-phenylglycine, but are not limited thereto.

According to the present invention, the microorganism may be selected from the group consisting of bacteria, yeast, and fungi, and preferably, the bacteria are selected from the group consisting of the genus *Corynebacterium* and *E. coli*., and more preferably *E. coli*, but any microorganism capable of producing an amino acid as a precursor or using the same as a carbon source may be used, without particular limitation thereto.

In another aspect, the present invention is directed to a method of preparing a primary amine including (a) culturing the mutant microorganism to produce a primary amine, and (b) collecting the produced primary amine.

In an embodiment of the present invention, in order to determine whether or not amino acids are converted into various primary amines using a mutant microorganism, a pTac15k_vlmD vector in which the gene vlmD encoding valine decarboxylase was cloned was produced (FIG. 5), and was then inserted into *E. coli* WL3110 (Lee et al., *Mol. Syst. Biol.* 3:1, 2007). In addition, in order to supply the precursor amino acid into the microorganism, the amino acid was fed as a carbon source along with glucose. The amino acid added herein is L-alanine, L-2-aminobutyrate, 2-aminobutyrate, L-norvaline, L-valine, L-isovaline, L-leucine, L-isoleucine, 1-aminocyclopentanecarboxylic acid or 1-aminocyclohexanecarboxylic acid. The mutant microorganism was grown under the above culture conditions. The result showed that ethylamine, propylamine, isopropylamine, butylamine, isobutylamine, (R)-sec-butylamine, isoamylamine, methylbutylamine, cyclopentylamine and cyclohexylamine were detected, depending on the amino acid added to the microorganism culture medium (FIG. 6).

In addition, according to an embodiment of the present invention, it was found that the modified microorganism according to the present invention converts L-alanine, L-2-aminobutyrate, 2-aminobutyrate, L-norvaline, L-valine, L-isovaline, L-leucine, L-isoleucine, 1-aminocyclopentanecarboxylic acid or 1-aminocyclohexanecarboxylic acid to ethylamine, propylamine, isopropylamine, butylamine, isobutylamine, (R)-sec-butylamine, isoamylamine, 2-methylbutylamine, cyclopentylamine and cyclohexylamine. However, examples of other primary amines that can be produced from various amino acids include methylamine, amylamine, benzylamine and the like, and the present invention is not limited with regard thereto.

Figure 9:
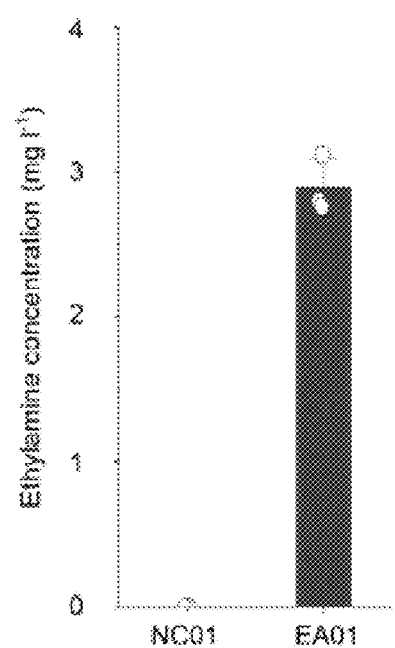
FIG. 9 is a graph showing whether ethylamines are produced from glucose in vivo using a mutant microorganisms transformed with the vlmD gene.
Figure 10:
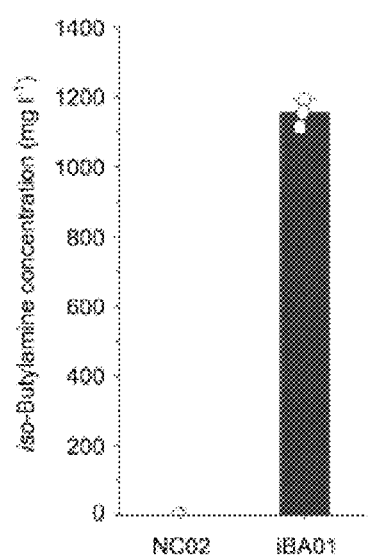
FIG. 10 is a graph showing whether or not isobutylamine is produced from glucose in vivo using the mutant microorganism transformed with the vlmD gene.
Figure 11:
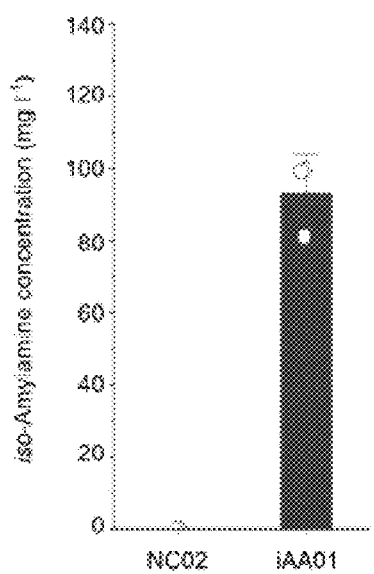
FIG. 11 is a graph showing whether or not isoamylamine is produced from glucose in vivo using the mutant microorganisms transformed with the vlmD gene.

In the present invention, when culturing the mutant microorganism to produce the primary amine, the culture may be conducted by adding an amino acid as a substrate, or the primary amine may be produced using an amino acid biosynthesized by the mutant microorganism. In order to verify this, in one embodiment of the present invention, a pTac15k_vlmD_alaD vector in which the vlmD gene encoding valine decarboxylase and the alaD gene encoding L-alanine dehydrogenase were cloned was produced (FIG. 7), and was then introduced into *E. coli* WL3110. The mutant microorganism was cultured in the presence of only glucose as a carbon source, without amino acids, and ethylamine was detected in the culture medium (FIG. 9). In another embodiment of the present invention, a pTac15k_vlmD vector in which the gene vlmD encoding valine decarboxylase was cloned was constructed (FIG. 5), and was then introduced into *E. coli* Val (pKBRilvBNCED) (Park et al., *Proc. Natl. Acad. Sci. USA.* 104:7797-7802, 2007). The mutant microorganism was cultured in a medium containing only glucose as a carbon source, without amino acids. The result showed that isobutylamine was detected in the microorganism culture medium (FIG. 10). Finally, a pTac15k_vlmD_pTac_leuABCD vector in which the gene vlmD encoding valine decarboxylase and the leuABCD gene encoding the L-leucine biosynthetic metabolic circuit were cloned was constructed (FIG. 8), and was then introduced into *E. coli* Val (pKBRilvBNCED). The mutant microorganism was cultured in only glucose as a carbon source, without amino acids. The result showed that isoamylamine was detected in the microbial culture solution (FIG. 11).

Any microorganism may be used in the present invention without limitation, as long as it is capable of producing an amino acid, and the microorganism may be *E. coli, Corynebacterium* genus, *Bacillus* genus, lactic acid bacteria or the like.

With regard to examples of the microorganism producing amino acids in the present invention, the microorganism producing L-alanine may be *E. coli* XZ132 (Zhang et al., *Appl. Microbiol. Biotechnol.* 77:355-366 2007) or the like, the microorganism producing L-2-aminobutyrate may be *E. coli* ATCC98082 (pZElac_tdcB_GDH) (Zhang et al., *Proc. Natl. Acad. Sci. USA.* 107:6234-6239, 2010), the microorganism producing L-norvaline may be B7 ΔilvBN ΔilvGM ΔilvIH (Sycheva et al., *Microbiology* 76:712-718, 2007), the microorganism producing L-valine may be *E. coli* Val (pKBRilvBNCED), *Corynebacterium glutamicum* WCC003/pJYW-4-ilvBNC1-lrp1-brnFE (Chen et al., *Metab. Eng.* 29:66-75, 2015), or the like, the microorganism producing L-norleucine may be *E. coli* B7 ΔilvBN ΔilvGM ΔilvIH/pBR-leuABCD (Sycheva et al., *Microbiology* 76:712-718, 2007), *E. coli* BWEC14 {pLEUfbr pOYE} (Anderhuber et al., *J. Biotechnol.* 235:100-111, 2016), or the like, the microorganism producing L-leucine may be *Corynebacterium glutamicum* MV-LeuF2 (Vogt et al., *Metab. Eng.* 22:40-52, 2014), *Corynebacterium glutamicum* MDLeu-19/pZ8-1/leuAr (Qingeng et al., *African J. Biotechnol.* 16:1048-1060, 2017), or the like, the microorganism producing L-isoleucine may be *E. coli* ILE03 (Park et al., *ACS Synth. Biol.* 1:53 2-540), *Corynebacterium glutamicum* JHI3-156 (Yin et al., *Metab. Eng.* 14:542-550), or the like, and the microorganism producing L-2-phenylglycine may be *E. coli* BC (pBPSPT and pUCSOT) (Liu et al., *J. Biotechnol.* 186:91-97, 2014) or the like.

According to the present invention, the process of culturing the mutant microorganism may be performed using a conventionally known culture method, and in addition to the specific medium and specific cultivation method used in the embodiments of the present invention, a saccharified solution such as whey or CSL (corn steep liquor) and other media may be used, and various methods such as fed-batch culture and continuous culture may be used (Lee et al., *Bioprocess Biosyst. Eng.*, 26: 63, 2003; Lee et al., *Appl. Microbiol. Biotechnol.*, 58: 663, 2002; Lee et al., *Biotechnol. Lett.*, 25: 111, 2003; Lee et al., *Appl. Microbiol. Biotechnol.*, 54: 23, 2000; Lee et al., *Biotechnol. Bioeng.*, 72: 41, 2001).

In another aspect, the present invention is directed to a method of preparing a primary amine including (a) reacting a valine decarboxylase with an amino acid to produce a primary amine, and (b) collecting the produced primary amine.

In an embodiment of the present invention, an enzyme activity assay was conducted to determine whether or not valine decarboxylase acts on amino acids, such as L-alanine, L-2-aminobutyrate, 2-aminoisobutyrate, L-norvaline, L-isovaline, L-norleucine, L-leucine, L-isoleucine, 1-aminocyclopentanecarboxylic acid, 1-aminocyclohexeningcarboxylic acid and L-2-phenylglycine, other than L-valine, which is a natural substrate.

First, in order to obtain a purified enzyme, the his-vlmD gene encoding the his-tagged valine decarboxylase was cloned to construct a pET22b_his_vlmD vector (FIG. 2), and the his-tagged valine decarboxylase was purified (FIG.

Figure 4:
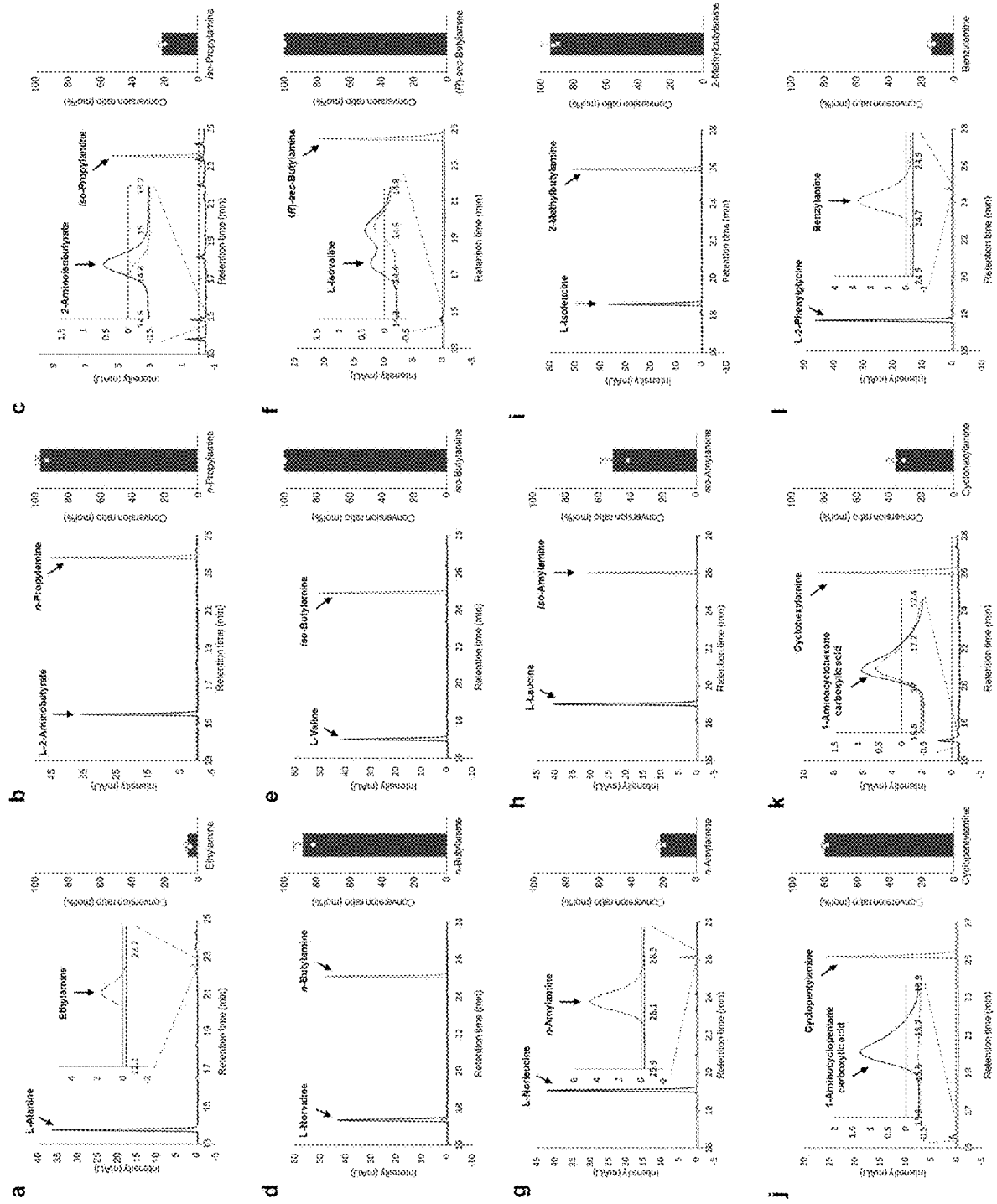
FIG. 4 shows the result of analysis of enzymatic activity of valine carboxylase and the result of HPLC showing the production of various primary amines using amino acids as substrates.

3). An enzyme assay was conducted using purified protein, pyridoxal phosphate (PLP), and L-alanine, L-2-aminobutyrate, 2-aminobutyrate, L-norvaline, L-valine, L-isovaline, L-norleucine, L-leucine, L-isoleucine, 1-aminocyclopentanecarboxylic acid, 1-aminocyclohexanecarboxylic acid, or L-2-phenylglycine. As a result, HPLC showed that a primary amine such as ethylamine, propylamine, isopropylamine, butylamine, isobutylamine, (R)-sec-butylamine, amylamine, isoamylamine, 2-methylbutylamine, cyclopentylamine, cyclohexylamine or benzylamine was produced (FIG. 4).

In addition, in an embodiment of the present invention, it was found that ethylamine, propylamine, isopropylamine, butylamine, isobutylamine, (R)-sec-butylamine, amylamine, isoamylamine, 2-methylbutylamine, cyclopentylamine, cyclohexylamine and benzylamine were produced using valine decarboxylase according to the present invention, but examples of primary amines that can be produced using various other amino acids as substrates may include methylamine, hexylamine and the like.

As used herein, the term "vector" means a DNA product containing a DNA sequence operably linked to a control sequence capable of expressing DNA in a suitable host. The vector may be a plasmid, a phage particle or a simple potential genome insert. Once the vector is transformed with an appropriate host, it may replicate and function independently of the genome of the host, or may often be integrated with the genome itself. Since the plasmid is the most commonly used type of vector, the terms "plasmid" and "vector" may be used interchangeably throughout the specification of the present invention. However, the present invention includes other forms of vectors having identical functions to those already known or to be known in the art. Typical expression vectors for mammalian cell culture expression are based on, for example, pRK5 (EP 307,247), pSV16B (WO 91/08291) and pVL1392 (Pharmingen).

As used herein, the term "expression control sequence" means a DNA sequence essential for the expression of a coding sequence operably linked to a particular host organism. Such a control sequence includes promoters for conducting transcription, operator sequences for controlling such transcription, sequences for encoding suitable mRNA ribosome-binding sites, and sequences for controlling the termination of transcription and translation. For example, control sequences suitable for prokaryotes include promoters, optional operator sequences and ribosome-binding sites. Eukaryotic cells include promoters, polyadenylation signals and enhancers. The factor that has the greatest impact on the expression level of the gene in the plasmid is a promoter. SRα promoters, cytomegalovirus-derived promoters and the like are preferably used as promoters for high expression.

Any of a wide variety of expression control sequences may be used for the vector in order to express the DNA sequences of the present invention. Useful expression control sequences include, for example, the early and late promoters of SV40 or adenovirus, the lac system, the trp system, the TAC or TRC system, T3 and T7 promoters, the major operator and promoter regions of phage lambda, control regions of fd code proteins, promoters of 3-phosphoglycerate kinase or other glycol lyases, promoters of phosphatase, such as Pho5, promoters of yeast alpha-mating systems and other sequences having configurations and inductions known to control the expression of genes of prokaryotic or eukaryotic cells or viruses thereof, and various combinations thereof. The T7 RNA polymerase promoter 010 may be useful for expressing proteins in $E.\ coli$.

When a nucleic acid sequence is aligned with another nucleic acid sequence based on a functional relationship, it is said to be "operably linked" thereto. This may be gene(s) and control sequence(s) linked in such a way so as to enable gene expression when a suitable molecule (e.g., a transcriptional activator protein) is linked to the control sequence(s). For example, DNA for a pre-sequence or secretory leader is operably linked to DNA for a polypeptide, when expressed as a pre-protein involved in the secretion of the polypeptide; a promoter or enhancer is operably linked to a coding sequence when it affects the transcription of the sequence; a ribosome-binding site is operably linked to a coding sequence when it affects the transcription of the sequence; or a ribosome-binding site is operably linked to a coding sequence when positioned to facilitate translation. Generally, "operably linked" means that the linked DNA sequence is in contact therewith, or that a secretory leader is in contact therewith and is present in the reading frame. However, the enhancer need not be in contact therewith. The linkage of these sequences is carried out by ligation (linkage) at convenient restriction enzyme sites. When no such site exists, a synthetic oligonucleotide adapter or a linker according to a conventional method is used.

As used herein, the term "expression vector" commonly refers to a recombinant carrier, into which a fragment of heterologous DNA is inserted, and generally means a fragment of double-stranded DNA. Herein, the heterologous DNA is xenogenous DNA that is not naturally found in the host cell. Once an expression vector is present in a host cell, it can replicate independently of the host chromosomal DNA, and several copies of the vector and inserted (heterologous) DNA thereof can be produced.

As is well known in the art, in order to increase the expression level of a transgene in a host cell, the gene should be operably linked to a transcriptional/translational expression control sequence that functions in a selected expression host. Preferably, the expression control sequence and the corresponding gene are included in one recombinant vector containing both a bacterial selection marker and a replication origin. When the expression host is a eukaryotic cell, the recombinant vector should further include a useful expression marker in the eukaryotic expression host.

A wide variety of expression host/vector combinations can be used to express the DNA sequences of subject proteins of the invention. Suitable expression vectors for eukaryotic hosts include, for example, expression control sequences derived from SV40, cow papillomavirus, adenovirus, adeno-associated virus, cytomegalovirus and retrovirus. Expression vectors that can be used for bacterial hosts include bacterial plasmids, exemplified by those obtained from $E.\ coli$, such as pBlueScript, pGEX2T, pUC vectors, col E1, pCR1, pBR322, pMB9 and derivatives thereof, plasmids having a wide host range such as RP4, phage DNA exemplified by a wide variety of phage lambda derivatives such as λgt10, λgt11 and NM989, and other DNA phages such as M13 and filamentous single-stranded DNA phages. Expression vectors useful for yeast cells include 2μ plasmids and derivatives thereof. The vector useful for insect cells is pVL 941.

The host cell transfected or transformed with the recombinant vector described above constitutes another aspect of the present invention. As used herein, the term "transfection" means introducing DNA into a host and making the DNA replicable by an extrachromosomal factor or chromosomal integration. As used herein, the term "transformation" means that an expression vector is accommodated by the host cell, regardless of whether or not any coding sequence is actually expressed.

The host cell of the present invention may be a prokaryotic or eukaryotic cell. In addition, a host having high introduction efficiency of DNA and high expression efficiency of the introduced DNA is usually used. Examples of the host cell that can be used include well-known eukaryotic and prokaryotic hosts such as *E. coli, Pseudomonas, Bacillus, Streptomyces*, fungi and yeast, insect cells such as *Spodoptera frugiperda* (SF9), animal cells such as CHO and mouse cells, African green monkey cells such as COS 1, COS 7, BSC 1, BSC 40 and BMT 10, and tissue-cultured human cells. When the cDNA encoding the protein of the present invention is cloned, it is preferable to use an animal cell as a host. In the present invention, CHSE-214, FHM, RTG-2 and EPC, derived from fish, are exemplified, but the present invention is not limited thereto. When COS cells are used, SV40 large T antigen is expressed in the COS cells. Therefore, a plasmid having a replication origin of SV40 is present as multiple episome copies in the cells, so higher expression can be expected. The introduced DNA sequence may be obtained from the same species as the host cell, may be a different species from the host cell, or may be a hybrid DNA sequence including any heterologous or homologous DNA.

It should be understood that not all vectors function identically in expressing the DNA sequences of the present invention. Likewise, not all hosts function identically for the same expression system. However, those skilled in the art will be able to make appropriate selections from among a variety of vectors, expression control sequences and hosts without excessive burden of experimentation and without departing from the scope of the present invention. For example, selection of a vector should be carried out in consideration of a host because the vector should be replicated therein. The number of replications of the vector, the ability to control the number of replications, and the expression of other proteins encoded by the corresponding vector, such as the expression of antibiotic markers, should also be considered. In selecting the expression control sequence, a number of factors should be considered. For example, the relative strength of the sequence, controllability, and compatibility with the DNA sequences of the present invention should be considered, particularly in relation to possible secondary structures. A single-cell host may be selected in consideration of factors such as the selected vector, the toxicity of the product encoded by the DNA sequence of the present invention, secretion characteristics, the ability to accurately fold proteins, culture and fermentation factors, and ease of purification of the product encoded by the DNA sequence according to the present invention. Within the scope of these factors, those skilled in the art can select various vector/expression control sequence/host combinations capable of expressing the DNA sequences of the present invention in fermentation or large animal cultures. As a screening method for cloning cDNA of proteins through expression cloning, a binding method, a panning method, a film emulsion method or the like can be applied.

Hereinafter, the present invention will be described in more detail with reference to the following examples. However, it will be obvious to those skilled in the art that the following examples are provided only for illustration of the present invention and should not be construed as limiting the scope of the present invention.

In particular, in the following examples, *E. coli* WL3110 or Val (pKBRilvBNCED) is used as a host microorganism. However, it will be obvious to those skilled in the art that other *E. coli*, bacteria, yeast, and fungi may also be used without particular limitation so long as they are capable of producing the precursor amino acids themselves or use the same as a carbon source. In addition, it will also be obvious to those skilled in the art that, although only genes derived from specific strains are exemplified as genes to be introduced in the following examples, any genes may be used without particular limitation, as long as they are expressed in host cells into which they are introduced and exhibit the same activity.

Example 1

Purification of Valine Decarboxylase
1-1: Production of pET22b_his_vlmD Vector

PCR was performed using linear DNA having a codon-optimized vlmD gene (SEQ ID NO: 3) synthesized to facilitate expression in *E. coli* from the vlmD gene (SEQ ID NO: 2) derived from a *Streptomyces viridifaciens* strain (Cosmogenetech, Seoul, Korea) as a template and the primers of SEQ ID NOS: 4 and 5 to obtain a his_vlmD gene fragment encoding a valine decarboxylase with a his-tag at the N terminus.

[SEQ ID NO: 4] vlmD_opt_His6(NdeI,F):
5'-AGACAGCATATGCATCATCACCATCACCACAGTACCAGCTCTGCCA
GTTCC-3'

[SEQ ID NO: 5] vlmD_opt_His6(EcoRI,R):
5'-AGACAGGAATTCTTAGCTGCCACCGCCATC-3'

Figure 2:
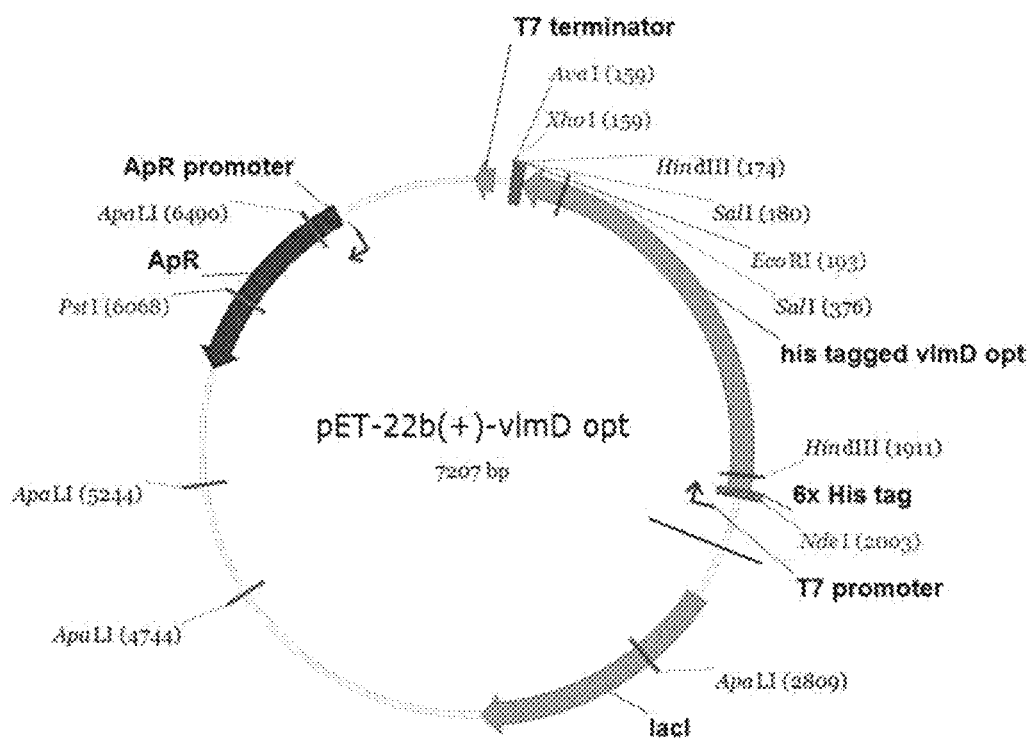
FIG. 2 shows the pET22b his-vlmD-overexpressing plasmid into which the his-tagged vlmD gene used to purify valine carboxylase is inserted.

Next, a pET22b(+) plasmid showing strong gene expression due to the T7 promoter was treated with restriction enzymes (NdeI and EcoRI), and was then treated with the obtained his_vlmD fragment and T4 DNA ligase, followed by ligation to produce a recombinant plasmid, pET22b his_vlmD (FIG. 2).

1-2: Purification of Valine Decarboxylase

For purification of valine decarboxylase, the plasmid pET22b_his_vlmD obtained in Example 1-1 was introduced into *E. coli* BL21(DE3) (F-ompT hsdSB(rB- mB-) gal dcm (DE3), a prophage carrying the T7 RNA polymerase gene). (New England Biolabs, USA). Transformed strains were inoculated in 10 mL of a LB liquid medium containing 25 mg/L of kanamycin (10 g/L of tryptone, 5 g/L of a yeast extract, 10 g/L of NaCl) and were initially cultured with continuous shaking at 37° C. at 200 rpm. Then, 1% of the strains was inoculated in 200 mL of the same medium and cultured with continuous shaking at 37° C. at 200 rpm.

Figure 3:
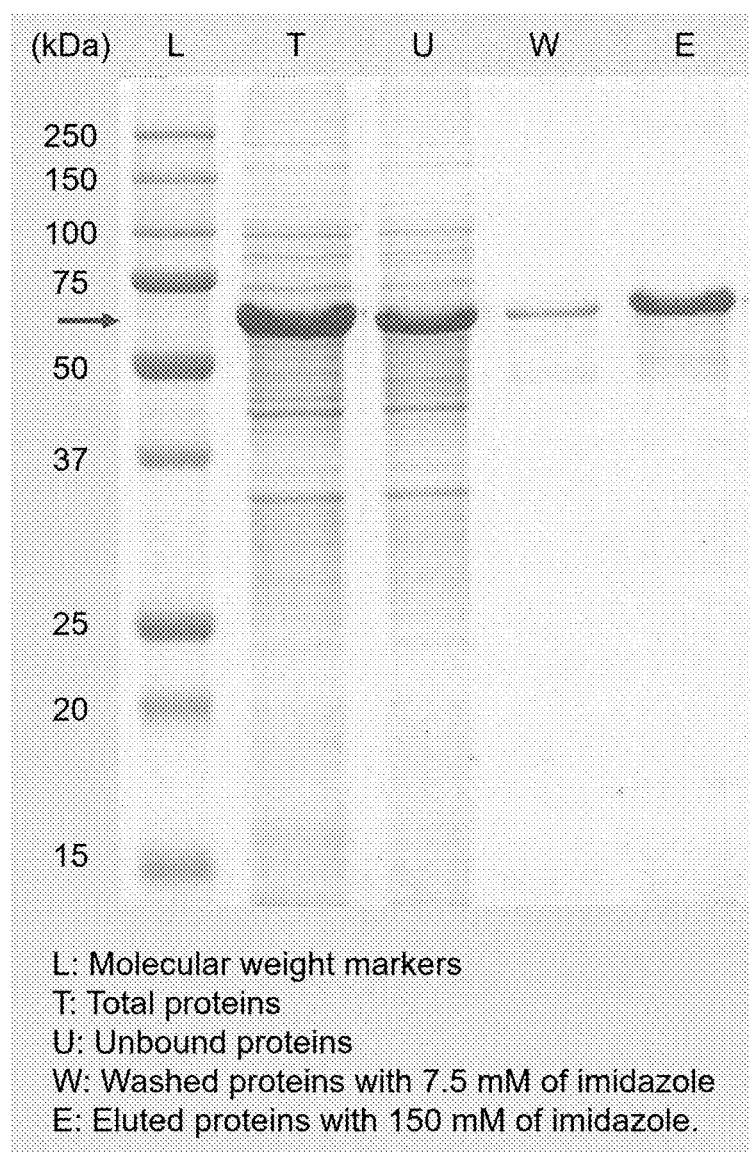
FIG. 3 is an image showing the result of SDS-PAGE of a fraction containing purified valine carboxylase.

Then, the O.D. of the culture solution was measured at a wavelength of 600 nm with a spectrophotometer, and when O.D. was 0.4, IPTG was added at 1 mM to induce his_vlmD expression and conduct culture again. 4 hours after induction of expression, the culture solution was centrifuged at 3,000 rpm and at 4° C. for 10 minutes, after which the microorganisms were separated and the supernatant was removed. Then, the separated microorganisms were suspended in 40 mL of equilibrium buffer (50 mM $Na_3PO_4$, 300 mM NaCl, pH 7.0), and then the microorganisms were disrupted for 2 hours by applying a pulse for 5 seconds at 30% intensity using a cell ultrasonicator and then allowing to stand for 5 seconds. Then, centrifugation was performed at 13,200 rpm at 4° C. for 10 minutes to remove cell debris and thereby to obtain a cell lysate. The cell lysate was filtered through a 0.45 μm filter to remove impurities, and then his-tagged valine decarboxylase was isolated therefrom using Talon resin. First, washing was performed with an equilibrium buffer containing 7.5 mM imidazole to remove impurities attached to the Talon resin. Then, the valine decarboxylase was separated by fractionation using an equilibrium buffer containing 150 mM imidazole. Then, all of the whole cell lysate, the protein solution having passed through the talon resin, and the protein solution obtained with each concentration of imidazole were mixed with 5× Laemmli sample buffer, followed by separation using 12% SDS-PAGE and staining with Coomassie brilliant blue R250 (Bio-Rad, USA) solution (FIG. 3). As a result, the valine decarboxylase purified at the highest purity of 120 mM was used as an enzyme solution, which was then used for the enzyme activity assay.

Example 2

Enzymatic Activity Assay of Valine Decarboxylase

An enzymatic activity assay was performed using a 50 mM potassium phosphate buffer (pH 7.5), and the substrate and enzyme used for the assay were added in the following amounts to the enzyme reaction solution.

Amino acids used as substrates were used at a concentration of 1 mM, and the amino acids used herein were L-alanine, L-2-aminobutyrate, 2-aminoisobutyrate, L-norvaline, L-valine, L-isovaline, L-norleucine, L-leucine, L-isoleucine, 1-aminocyclopentanecarboxylic acid, 1-aminocyclohexanecarboxylic acid, and L-2-phenylglycine. 0.1 mM pyridoxal phosphate (PLP) and 150 µg of the purified valine decarboxylase were added, followed by conducting reaction at 37° C. for 2 hours, and the sample after the reaction was analyzed by HPLC to identify primary amine.

As can be seen from FIG. 4, the result of HPLC analysis performed using, as substrates, L-alanine, L-2-aminobutyrate, 2-aminoisobutyrate, L-norvaline, L-valine, L-isovaline, L-norleucine, L-leucine, L-isoleucine, 1-aminocyclopentanecarboxylic acid, 1-aminocyclohexanecarboxylic acid, and L-2-phenylglycine showed that peaks corresponding to ethylamine, n-propylamine, iso-propylamine, n-butylamine, iso-butylamine, (R)-sec-butylamine, n-amylamine, iso-amylamine, 2-methylbutylamine, cyclopentylamine, cyclohexylamine and benzylamine were detected (FIG. 4).

Primary amine production was analyzed using HPLC (1100 Series HPLC; Agilent Technologies, Santa Clara, CA). The primary amine derivatization for analysis was performed in an automatic manner before analysis using an o-phthaldialdehyde (OPA; Sigma, St. Louis, MO) reagent. The OPA reagent for derivatization was prepared by dissolving 0.20 g of OPA reagent in 9.0 mL of methanol and then adding 1.0 mL of 0.40 M (pH 9.0) borate buffer and 160 µL of 2-mercaptoethanol thereto. For derivatization, 1 µL of the sample was mixed with 5 µL of 0.40 M (pH 9.0) borate buffer. Then, 1 µL of the OPA reagent for derivatization prepared above was added thereto, followed by HPLC analysis. Analysis was performed at 25° C. using an Eclipse plus C18 column (4.6×150 mm; Agilent Technologies). Solvent A for analysis was prepared by mixing 1.4 g/L of $Na_2HPO_4$ and 3.8 g/L of $Na_2B_4O_7 \cdot 10H_2O$ with 8 mg/L of $NaN_3$, and adjusting the final pH of the resulting mixture to 7.2 using HCl. Solvent B was prepared by mixing 45% acetonitrile and 45% methanol with 10% $H_2O$ based on volume %. The solvent was fed at a rate of 2 mL/min. Solvents A and B were fed at the following rates for each time: solvent A was fed at a rate of 100% at 0-0.5 minutes, the flow of solvent B increased linearly from 0% to 57% at 0.5-18 minutes, the flow of solvent B linearly increased from 57% to 100% at 18-26 minutes, solvent B flowed at a rate of 100% at 26-29 minutes, and finally, the flow of solvent B linearly decreased from 100% to 0% at 29-minutes. The derivatized secondary amines could be analyzed by detecting light with a wavelength of 230 nm using a variable wavelength detector (G1314A; Agilent Technologies).

The results above showed that the valine decarboxylase obtained in Example 1 successfully converted L-alanine, L-2-aminobutyrate, 2-aminobutyrate, L-norvaline, L-valine, L-isovaline, L-norleucine, L-leucine, L-isoleucine, 1-aminocyclopentanecarboxylic acid, 1-aminocyclohexanecarboxylic acid and L-2-phenylglycine to ethylamine, propylamine, isopropylamine, butylamine, isobutylamine, (R)-sec-butylamine, amylamine, isoamylamine, 2-methylbutylamine, cyclopentylamine, cyclohexylamine and benzylamine, respectively.

Example 3

Production of pTac15k_vlmD Vector

PCR was performed using linear DNA (Cosmogenetech, Seoul, Korea) having a codon-optimized vlmD gene (SEQ ID NO: 3) synthesized to facilitate expression in *E. coli* as a template and primers of SEQ ID NOS: 6 and 7 to obtain a vlmD gene fragment encoding a valine decarboxylase.

[SEQ ID NO: 6] vlmD_opt(EcoR1,F1):
5'-AGACAGGAATTCATGTCAACTTCCTCCGCTTCTTCCG-3'

[SEQ ID NO: 7] vlmD_opt(KpnI,R1):
5'-AGACAGGGTACCTCAGCTCCCGCCGCCGT-3'

Figure 5:
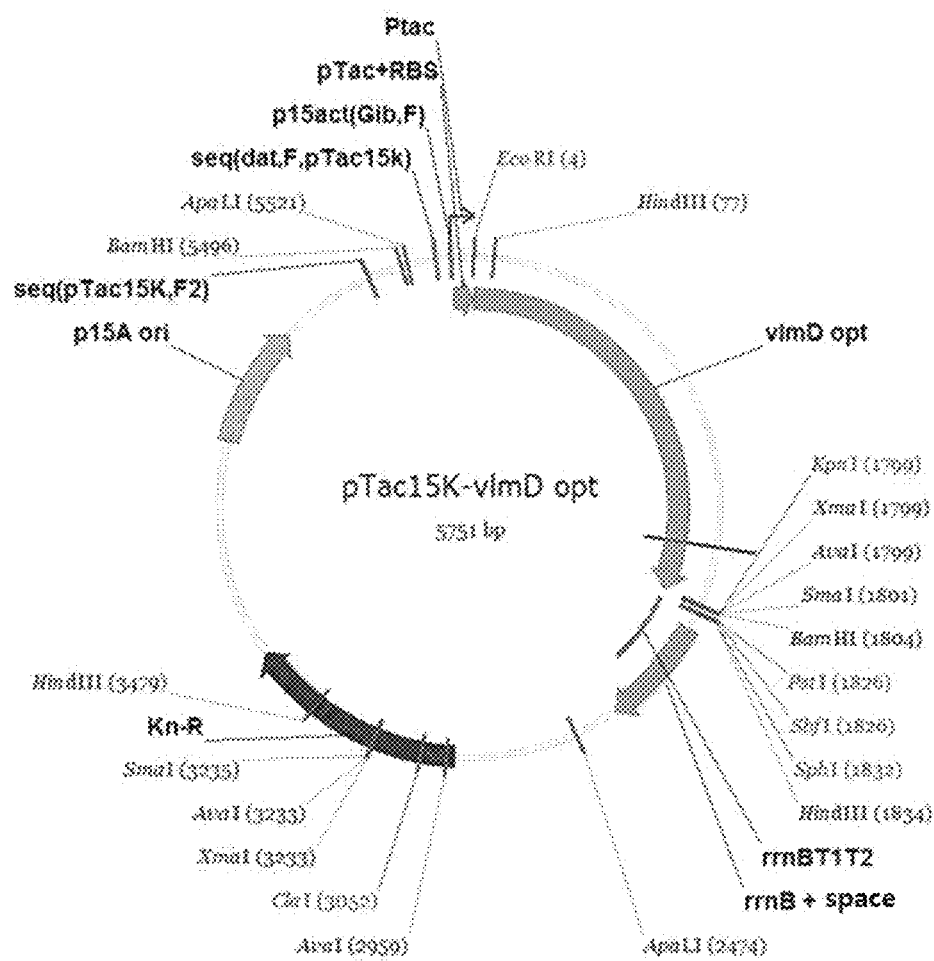
FIG. 5 shows the pTac15_k_vlmD plasmid into which the vlmD gene used to produce primary amines in vivo using a mutant microorganism is inserted.
Figure 6:
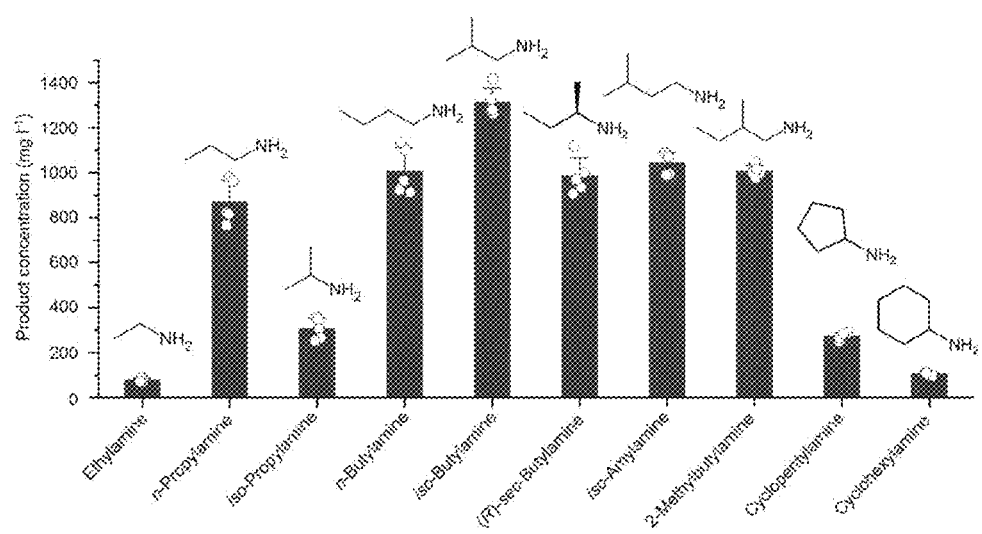
FIG. 6 is a graph showing whether or not various primary amines are produced from various amino acids in vivo using a mutant microorganism transformed with the vlmD gene.

Then, the pTac15k (Hiszczyńska-Sawicka and Kur, 1997) plasmid that strongly expresses the gene due to the tac promoter was treated with restriction enzymes (EcoRI and KpnI), and was then ligated with the obtained vlmD fragment using T4 DNA ligase to produce a recombinant plasmid pTac15k_vlmD (FIG. 5).

Example 4

Identification of Production of Various Types of Primary Amines from Amino Acids Using Mutant Microorganisms Expressing vlmD Gene Encoding Decarboxylase A mutant microorganism was constructed by introducing pTac15k_vlmD, the plasmid containing the vlmD gene encoding a decarboxylase, produced in Example 3, into *E. coli* WL3110, and whether or not the mutant microorganism produced a primary amine from an amino acid was identified.

*E. coli* WL3110, introduced with pTac15k as a blank vector, was used as a control.

Mutant microorganisms were selected in LB plate medium (10 g/L of tryptone, 5 g/L of a yeast extract, 10 g/L of NaCl) supplemented with 25 mg/L of kanamycin. The transformed strain was inoculated into 10 mL of a LB medium, followed by pre-culture at 37° C. for 8 hours. Then, 1.5 mL of the pre-cultured culture solution was inoculated into 50 mL of modified MR medium in a 350 mL flask, followed by culture.

The modified MR medium was a medium consisting of 10 g glucose, 6.67 g of $KH_2PO_4$, 4 g of $(NH_4)_2HPO_4$, 0.8 g $MgSO_4 \cdot 7H_2O$, 0.8 g of citric acid, and 5 ml of a trace metal solution with respect to 1 liter of distilled water. The trace metal solution consisted of 10 g of $FeSO_4 \cdot 7H_2O$, 2 g of $CaCl_2$, 2.2 g of $ZnSO_4 \cdot 7H_2O$, 0.5 g of $MnSO_4 \cdot 4H_2O$, 1 g of $CuSO_4 \cdot 5H_2O$, 0.1 g of $(NH_4)_6Mo_7O_{24} \cdot 4H_2O$ and 0.02 g of $Na_2B_4O_7 \cdot 10H_2O$ with respect to 1 liter of distilled water.

In addition, amino acids respectively used as precursors of primary amines were added at a concentration of 2 g/L, and the amino acids used herein were L-alanine, L-2-aminobutyrate, 2-aminoisobutyrate, L-norvaline, L-valine, L-isovaline, L-leucine, L-isoleucine, 1-aminocyclopentanecarboxylic acid, and 1-aminocyclohexanecarboxylic acid.

The culture was performed at 37° C. for 36 hours with shaking at 200 rpm. After the culture was completed, the culture solution was centrifuged at 13,200 rpm for 10 minutes, only the supernatant was collected, and HPLC analysis was performed in the same manner as in Example 2 to identify the production of primary amines.

As can be seen from FIG. 6, the mutant microorganism according to the present invention produced ethylamine, propylamine, isopropylamine, butylamine, isobutylamine, (R)-sec-butylamine, isoamylamine, 2-methylbutylamine, cyclopentylamine and cyclohexylamine.

Example 5

Production of pTac15k_vlmD_alaD Vector

PCR was performed using linear DNA (Cosmogenetech, Seoul, Korea) having a codon-optimized alaD gene (SEQ ID NO: 8) encoding L-alanine dehydrogenase derived from *Geobacillus stearothermophilus* synthesized to facilitate expression in *E. coli* as a template and primers of SEQ ID NOS: 9 and 10 to obtain an alaD gene fragment encoding alanine dehydrogenase.

[SEQ ID NO: 9] alaD_opt(KpnI,F1):
5'-AGACAGGGTACCTTTCACACAGGAAACAATGAAAATTGGTATACCG
AAGGAA-3'

[SEQ ID NO: 10] vlmD_opt(PstI,R1):
5'-AGACAGCTGCAGTCATCCTTGCAGAAGAGAATGGAAGCGAATTTTA
TCAGC-3'

Figure 7:
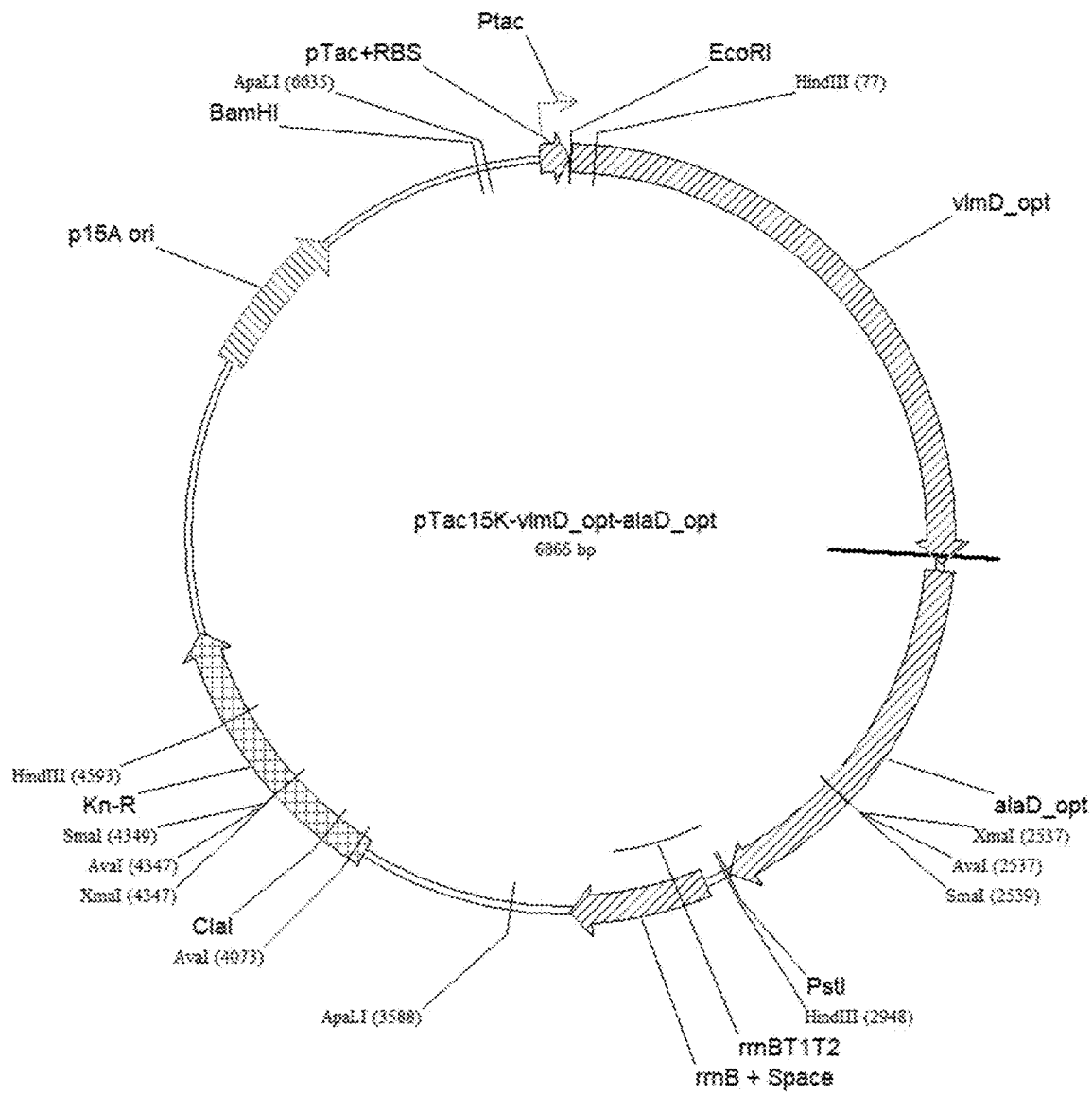
FIG. 7 shows the pTac15k_vlmD_alaD plasmid into which the vlmD and alaD genes, used to produce ethylamine from glucose in vivo using a mutant microorganism, are inserted.

Then, the pTac15k-vlmD plasmid produced in Example 3 was treated with restriction enzymes (KpnI and PstI) and then ligated with the obtained alaD fragment using T4 DNA ligase to produce a recombinant plasmid pTac15k_vlmD_alaD. (FIG. 7).

Example 6

Production of pTac15k_vlmD_pTac_leuABCD Vector

PCR was performed using the chromosomal DNA of the *Escherichia coli* strain (Coli Genetic Stock Center) as a template and the primers of SEQ ID NOS: 11 and 12, and PCR was performed again with the linear DNA thus obtained as a template and the primers of SEQ ID NOS: 13 and 14 to obtain a DNA fragment having both the tac promoter and the leuABCD gene encoding the leucine biosynthetic metabolic circuit.

[SEQ ID NO: 11] leuABCD(PstI,F1):
5'-GCTCGTATAATGTGTGGAATTGTGAGCGGATAACAATTTCACACAGG
AAACAATGAGCCAGCAAGTCATTATTTT-3'

[SEQ ID NO: 12] leuABCD(PstI,R1):
5'-TTAATTCATAAACGCAGGTTGTTT-3'

[SEQ ID NO: 13] leuABCD(PstI,F2):
5'-AGACAGCTGCAGGCTGTTGACAATTAATCATCGGCTCGTATAATGTG
TGGAATTGTG-3'

[SEQ ID NO: 14] leuABCD(PstI,R2):
5'-AGACAGCTGCAGTTAATTCATAAACGCAGGTTGTTTTGTCCGAGCCG
GAAGAG-3'

Figure 8:
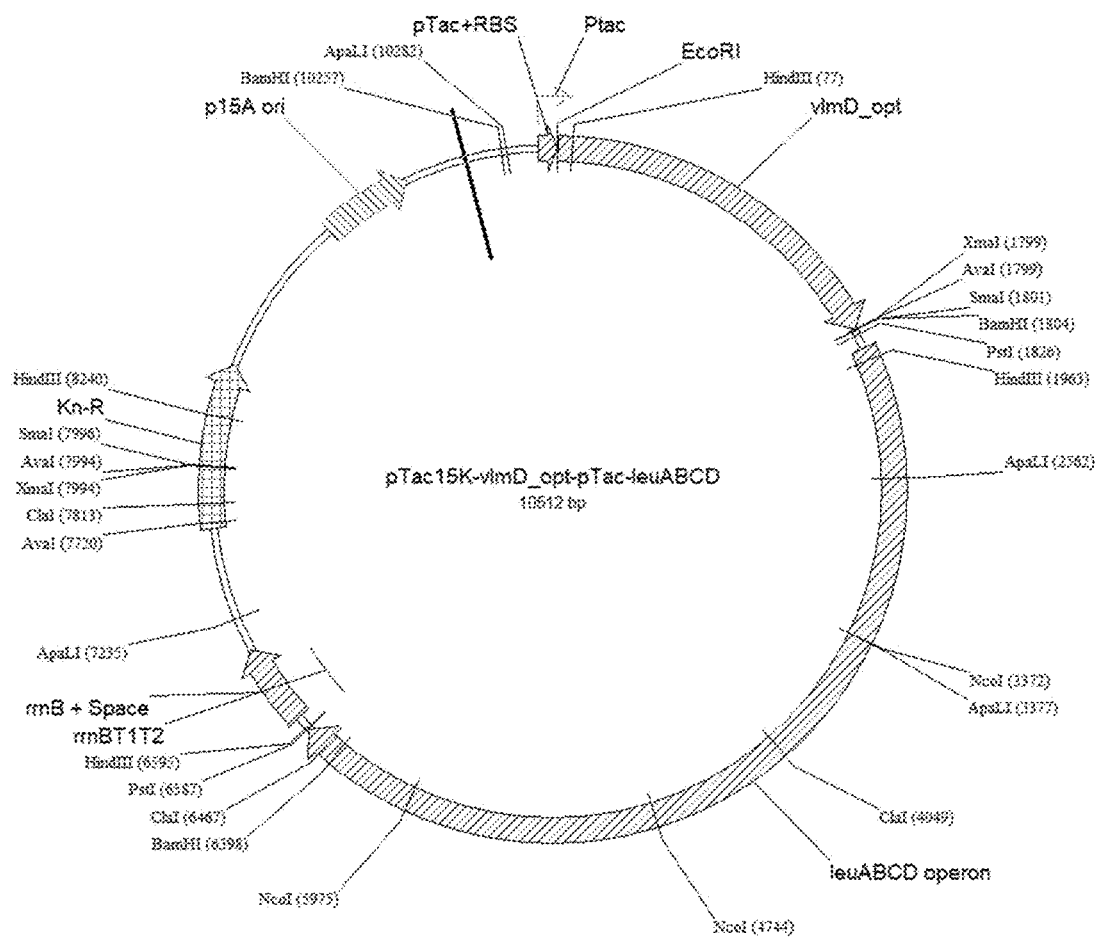
FIG. 8 shows the pTac15k_vlmD_pTac_leuABCD plasmid into which the vlmD and leuABCD genes, used to produce isoamylamine from glucose in vivo using a mutant microorganism, are inserted.

Then, the pTac15k-vlmD plasmid produced in Example 3 was treated with a restriction enzyme (PstI), and was then ligated with the obtained pTac_leuABCD fragment using T4 DNA ligase to produce a recombinant plasmid pTac15k_vlmD_pTac-leuABCD (FIG. 8).

Example 7

Identification of Production of Various Types of Primary Amines from Glucose Using Mutant Microorganisms Expressing vlmD Gene Encoding Decarboxylase 7-1: Identification of Production of Ethyl Amine from Glucose Using Mutant Microorganism Expressing vlmD Gene Encoding Decarboxylase A mutant microorganism was constructed by introducing pTac15k_vlmD_alaD, the plasmid containing the vlmD gene encoding a decarboxylase and the alaD gene encoding an alanine dehydrogenase, produced in Example 5, into *E. coli* WL3110, and whether or not the mutant microorganism produced primary amine from glucose was identified.

*E. coli* WL3110, introduced with pTac15k as a blank vector, was used as a control.

Mutant microorganisms were selected in LB plate medium (10 g/L of tryptone, 5 g/L of a yeast extract, 10 g/L of NaCl) supplemented with 25 mg/L of kanamycin. The transformed strain was inoculated into 10 mL of a LB medium, followed by pre-culture at 37° C. for 8 hours. Then, 1.5 mL of the pre-cultured culture solution was inoculated into 50 mL of modified MR medium in a 350 mL flask, followed by culture.

The modified MR medium was a medium consisting of 20 g of glucose, 6.67 g of $KH_2PO_4$, 4 g of $(NH_4)_2HPO_4$, 0.8 g of $MgSO_4·7H_2O$, 0.8 g of citric acid, and 5 ml of a trace metal solution with respect to 1 liter of distilled water. The trace metal solution consisted of 10 g of $FeSO_4·7H_2O$, 2 g of $CaCl_2$, 2.2 g of $ZnSO_4·7H_2O$, 0.5 g of $MnSO_4·4H_2O$, 1 g of $CuSO_4·5H_2O$, 0.1 g of $(NH_4)_6Mo_7O_{24}·4H_2O$ and 0.02 g of $Na_2B_4O_7·10H_2O$ with respect to 1 liter of distilled water.

The culture was performed at 37° C. for 36 hours with shaking at 200 rpm. After the culture was completed, the culture solution was centrifuged at 13,200 rpm for 10 minutes, only the supernatant was collected and HPLC analysis was performed in the same manner as in Example 2 to identify the production of ethyl amine.

As can be seen from FIG. 9, the mutant microorganism transformed with the blank vector as a control did not produce ethylamine, whereas the mutant microorganism according to the present invention produced 76.28 mg/L of ethylamine from glucose.

7-2: Identification of Production of Isobutylamine from Glucose Using Mutant Microorganisms Expressing vlmD Gene Encoding Decarboxylase A mutant microorganism was constructed by introducing pTac15k_vlmD, the plasmid containing the vlmD gene encoding a decarboxylase, produced in Example 3, into *E. coli* Val (pKBRilvBNCED), and whether or not the mutant microorganism produced isobutylamine from glucose was identified.

*E. coli* Val (pKBRilvBNCED), introduced with pTac15k as a blank vector, was used as a control.

Mutant microorganisms were selected in LB plate medium (10 g/L of tryptone, 5 g/L of a yeast extract, 10 g/L of NaCl) supplemented with 25 mg/L of kanamycin. The transformed strain was inoculated into 10 mL of a LB medium, followed by pre-culture at 37° C. for 8 hours. Then, 1.5 mL of the pre-cultured culture solution was inoculated into 50 mL of NM2 medium in a 350 mL flask, followed by culture.

The NM2 medium consisted of 50 g of glucose, 30 g of CaCO$_3$, 12.5 g of (NH$_4$)$_2$SO$_4$, 4.0 g of KH$_2$PO$_4$, 2.0 g of MgSO$_4$·7H$_2$O, 2.0 g of a yeast extract, 0.262 g of L-isoleucine, 0.262 g of L-leucine, 0.425 mg of sodium D-pantothenate and 5 ml of a trace metal solution with respect to 1 liter of distilled water. The trace metal solution consisted of 10 g of FeSO$_4$·7H$_2$O, 2 g of CaCl$_2$, 2.2 g of ZnSO$_4$·7H$_2$O, 0.5 g of MnSO$_4$·4H$_2$O, 1 g of CuSO$_4$·5 H$_2$O, 0.1 g of (NH$_4$)$_6$Mo$_7$O$_{24}$·4H$_2$O and 0.02 g of Na$_2$B$_4$O$_7$·10H$_2$O with respect to 1 liter of distilled water.

The culture was performed at 30° C. for 48 hours with shaking at 200 rpm. After the culture was completed, the culture solution was centrifuged at 13,200 rpm for 10 minutes, only the supernatant was collected and HPLC analysis was performed in the same manner as in Example 2 to identify the production of isobutylamine.

As can be seen from FIG. 10, the mutant microorganism transformed with the blank vector as a control did not produce isobutylamine, whereas the mutant microorganism according to the present invention produced 1155.74 mg/L of isobutylamine from glucose.

7-3: Identification of Production of Isoamylamine from Glucose Using Mutant Microorganisms Expressing vlmD Gene Encoding Decarboxylase A mutant microorganism was constructed by introducing pTac15k_vlmD_pTac_leuABCD, the plasmid containing the vlmD gene encoding a decarboxylase and the leuABCD gene encoding the L-leucine biosynthetic metabolic circuit, produced in Example 5-2, into *E. coli* Val (pKBRilvBNCED), and whether or not the mutant microorganism produced isoamylamine from glucose was identified.

*E. coli* Val (pKBRilvBNCED), introduced with pTac15k as a blank vector, was used as a control.

Mutant microorganisms were selected in LB plate medium (10 g/L of tryptone, 5 g/L of a yeast extract, 10 g/L of NaCl) supplemented with 25 mg/L of kanamycin. The transformed strain was inoculated into 10 mL of a LB medium, followed by pre-culture at 37° C. for 8 hours. Then, 1.5 mL of the pre-cultured culture solution was inoculated into 50 mL of NM2 medium in a 350 mL flask, followed by culture.

The modified NM2 medium consisted of 50 g of glucose, 30 g of CaCO$_3$, 12.5 g of (NH$_4$)$_2$SO$_4$, 4.0 g of KH$_2$PO$_4$, 2.0 g of MgSO$_4$·7H$_2$O, 2.0 g of a yeast extract, 0.262 g of L-isoleucine, 0.262 g of L-leucine, 0.425 mg of sodium D-pantothenate and 5 ml of a trace metal solution with respect to 1 liter of distilled water. The trace metal solution consisted of 10 g of FeSO$_4$·7H$_2$O, 2 g of CaCl$_2$, 2.2 g of ZnSO$_4$·7H$_2$O, 0.5 g of MnSO$_4$·4H$_2$O, 1 g of CuSO$_4$·5 H$_2$O, 0.1 g of (NH$_4$)$_6$Mo$_7$O$_{24}$·4H$_2$O and 0.02 g of Na$_2$B$_4$O$_7$·10H$_2$O with respect to 1 liter of distilled water.

The culture was performed at 30° C. for 48 hours with shaking at 200 rpm. After the culture was completed, the culture solution was centrifuged at 13,200 rpm for 10 minutes, only the supernatant was collected and HPLC analysis was performed in the same manner as in Example 2 to identify the production of isoamylamine.

As can be seen from FIG. 11, the mutant microorganism transformed with the blank vector as a control did not produce isoamylamine, whereas the mutant microorganism according to the present invention produced 92.23 mg/L of isoamylamine from glucose.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

---

What is claimed is:

1. A mutant microorganism for use in producing ethylamine from a glucose, in which a gene comprising the sequence of SEQ ID NO: 3 encoding a valine decarboxylase and a gene comprising the sequence of SEQ ID NO: 8 encoding an L-alanine dehydrogenase are introduced into the mutant microorganism.

2. The mutant microorganism according to claim 1, wherein the microorganism is selected from the group consisting of bacteria, yeast, and fungi.

3. A method of preparing an ethylamine comprising:
   (a) culturing the mutant microorganism according to claim 1 to produce an ethylamine; and
   (b) collecting the produced ethylamine.

\* \* \* \* \*

UNITED STATES PATENT AND TRADEMARK OFFICE
CERTIFICATE OF CORRECTION

PATENT NO. : 12,104,192 B2
APPLICATION NO. : 17/194222
DATED : October 1, 2024
INVENTOR(S) : Sang Yup Lee et al.

Page 1 of 1

It is certified that error appears in the above-identified patent and that said Letters Patent is hereby corrected as shown below:

In the Specification

Column 3, Line 12, "pTac15_k_vlmD" should be -- pTac15k_vlmD --.

Column 7, Line 65, "010" should be -- Φ10 --.

Column 11, Line 67, "29-minutes" should be -- 29-30 minutes --.

Column 12, Line 30, "Hiszczyhska-Sawicka" should be -- Hiszczyńska-Sawicka --.

Signed and Sealed this
Twenty-second Day of April, 2025

Coke Morgan Stewart
*Acting Director of the United States Patent and Trademark Office*

SEQUENCE LISTING

```
<160> NUMBER OF SEQ ID NOS: 14

<210> SEQ ID NO 1
<211> LENGTH: 594
<212> TYPE: PRT
<213> ORGANISM: Artificial Sequence
<220> FEATURE:
<223> OTHER INFORMATION: valine decarboxylase of Streptomyces
      viridifaciens

<400> SEQUENCE: 1

Met Ser Thr Ser Ser Ala Ser Ser Gly Pro Asp Leu Pro Phe Gly Pro
1               5                   10                  15

Glu Asp Thr Pro Trp Gln Lys Ala Phe Ser Arg Leu Arg Ala Val Asp
                20                  25                  30

Gly Val Pro Arg Val Thr Ala Pro Ser Ser Asp Pro Arg Glu Val Tyr
            35                  40                  45

Met Asp Ile Pro Glu Ile Pro Phe Ser Lys Val Gln Ile Pro Pro Asp
        50                  55                  60

Gly Met Asp Glu Gln Gln Tyr Ala Glu Ala Glu Ser Leu Phe Arg Arg
65                  70                  75                  80

Tyr Val Asp Ala Gln Thr Arg Asn Phe Ala Gly Tyr Gln Val Thr Ser
                85                  90                  95

Asp Leu Asp Tyr Gln His Leu Ser His Tyr Leu Asn Arg His Leu Asn
                100                 105                 110
```

```
Asn Val Gly Asp Pro Tyr Glu Ser Ser Tyr Thr Leu Asn Ser Lys
            115                 120                 125

Val Leu Glu Arg Ala Val Leu Asp Tyr Phe Ala Ser Leu Trp Asn Ala
130                 135                 140

Lys Trp Pro His Asp Ala Ser Asp Pro Glu Thr Tyr Trp Gly Tyr Val
145                 150                 155                 160

Leu Thr Met Gly Ser Ser Gly Asn Leu Tyr Gly Leu Trp Asn Ala
                165                 170                 175

Arg Asp Tyr Leu Ser Gly Lys Leu Arg Arg Gln His Arg Glu Ala
            180                 185                 190

Gly Gly Asp Lys Ala Ser Val Val Tyr Thr Gln Ala Leu Arg His Glu
            195                 200                 205

Gly Gln Ser Pro His Ala Tyr Glu Pro Val Ala Phe Phe Ser Gln Asp
    210                 215                 220

Thr His Tyr Ser Leu Thr Lys Ala Val Arg Val Leu Gly Ile Asp Thr
225                 230                 235                 240

Phe His Ser Ile Gly Ser Ser Arg Tyr Pro Asp Glu Asn Pro Leu Gly
                245                 250                 255

Pro Gly Thr Pro Trp Pro Thr Glu Val Pro Ser Val Asp Gly Ala Ile
            260                 265                 270

Asp Val Asp Lys Leu Ala Ser Leu Val Arg Phe Phe Ala Ser Lys Gly
            275                 280                 285

Tyr Pro Ile Leu Val Ser Leu Asn Tyr Gly Ser Thr Phe Lys Gly Ala
            290                 295                 300

Tyr Asp Asp Val Pro Ala Val Ala Gln Ala Val Arg Asp Ile Cys Thr
305                 310                 315                 320

Glu Tyr Gly Leu Asp Arg Arg Val Tyr His Asp Arg Ser Lys Asp
                325                 330                 335

Ser Asp Phe Asp Glu Arg Ser Gly Phe Trp Ile His Ile Asp Ala Ala
            340                 345                 350

Leu Gly Ala Gly Tyr Ala Pro Tyr Leu Gln Met Ala Arg Asp Ala Gly
            355                 360                 365

Met Val Glu Glu Ala Pro Pro Val Phe Asp Phe Arg Leu Pro Glu Val
370                 375                 380

His Ser Leu Thr Met Ser Gly His Lys Trp Met Gly Thr Pro Trp Ala
385                 390                 395                 400

Cys Gly Val Tyr Met Thr Arg Thr Gly Leu Gln Met Thr Pro Pro Lys
                405                 410                 415

Ser Ser Glu Tyr Ile Gly Ala Ala Asp Thr Thr Phe Ala Gly Ser Arg
            420                 425                 430

Asn Gly Phe Ser Ser Leu Leu Leu Trp Asp Tyr Leu Ser Arg His Ser
            435                 440                 445

Tyr Asp Asp Leu Val Arg Leu Ala Ala Asp Cys Asp Arg Leu Ala Gly
            450                 455                 460

Tyr Ala His Asp Arg Leu Leu Thr Leu Gln Asp Lys Leu Gly Met Asp
465                 470                 475                 480

Leu Trp Val Ala Arg Ser Pro Gln Ser Leu Thr Val Arg Phe Arg Gln
                485                 490                 495

Pro Cys Ala Asp Ile Val Arg Lys Tyr Ser Leu Ser Cys Glu Thr Val
            500                 505                 510

Tyr Glu Asp Asn Glu Gln Arg Thr Tyr Val His Leu Tyr Ala Val Pro
            515                 520                 525

His Leu Thr Arg Glu Leu Val Asp Glu Leu Val Arg Asp Leu Arg Gln
```

```
                530               535               540
Pro Gly Ala Phe Thr Asn Ala Gly Ala Leu Glu Gly Glu Ala Trp Ala
545                 550               555               560

Gly Val Ile Asp Ala Leu Gly Arg Pro Asp Pro Asp Gly Thr Tyr Ala
                565               570               575

Gly Ala Leu Ser Ala Pro Ala Ser Gly Pro Arg Ser Glu Asp Gly Gly
            580               585               590

Gly Ser

<210> SEQ ID NO 2
<211> LENGTH: 1785
<212> TYPE: DNA
<213> ORGANISM: Artificial Sequence
<220> FEATURE:
<223> OTHER INFORMATION: valine decarboxylase of Streptomyces
      viridifaciens

<400> SEQUENCE: 2
gtgtcaactt cctccgcttc ttccgggccg gacctcccct cgggcccga ggacacgcca      60 tggcagaagg ccttcagcag gctgcgggcg gtggatggcg tgccgcgcgt caccgcgccg     120
tccagtgatc cgcgtgaggt ctacatggac atcccgagga tcccccttctc caaggtccag    180 atccccccgg acggaatgga cgagcagcag tacgcagagg ccgagagcct cttccgccgc     240
tacgtagacg cccagacccg caacttcgcg ggataccagg tcaccagcga cctcgactac     300
cagcacctca gtcactatct caaccggcat ctgaacaacg tcggcgatcc ctatgagtcc     360
agctcctaca cgctgaactc caaggtcctt gagcgagccg ttctcgacta cttcgcctcc     420
ctgtggaacg ccaagtggcc ccatgacgca agcgatccgg aaacgtactg gggttacgtg     480
ctgaccatgg gctccagcga aggcaacctg tacgggttgt ggaacgcacg ggactatctg     540
tcgggcaagc tgctgcggcg ccagcaccgg gaggccggcg cgacaaggc ctcggtcgtc      600 tacacgcaag cgctgcgaca cgaagggcag agtccgcatg cctacgagcc ggtggcgttc     660
ttctcgcagg acacgcacta ctcgctcacg aaggccgtgc gggttctggg catcgacacc     720
ttccacagca tcggcagcag tcggtatccg gacgagaacc cgctgggccc cggcactccg     780
tggccgaccg aagtgccctc ggttgacggt gccatcgatg tcgacaaact cgcctcgttg     840
gtccgcttct tcgccagcaa gggctacccg atactggtca gcctcaacta cgggtcaacg     900
ttcaagggcg cctacgacga cgtcccggcc gtggcacagg ccgtgcggga catctgcacg     960
gaatacggtc tggatcggcg gcgggtatac cacgaccgca gtaaggacag tgacttcgac    1020
gagcgcagcg gcttctggat ccacatcgat gccgccctgg gggcgggcta cgctccctac    1080
ctgcagatgg cccgggatgc cggcatggtc gaggaggcgc cgcccgtttt cgacttccgg    1140 ctccccggagg tgcactcgct gaccatgagc ggccacaagt ggatgggaac ccgtgggca    1200 tgcggtgtct acatgacacg gaccgggctg cagatgaccc cgccgaagtc gtccgagtac    1260
atcggggcgg ccgacaccac cttcgcgggc tcccgcaacg gcttctcgtc actgctgctg    1320
tgggactacc tgtcccggca ttcgtatgac gatctggtgc gcctggccgc cgactgcgac    1380
cggctggccg gctacgccca cgaccggttg ctgaccttgc aggacaaact cggcatggat    1440
ctgtgggtcg cccgcagccc gcagtccctc acggtgcgct ccgtcagcc atgtgcagac    1500 atcgtccgca agtactcgct gtcgtgtgag acggtctacg aagacaacga gcaacggacc    1560
tacgtacatc tctacgccgt tccccacctc actcgggaac tcgtggatga gctcgtgcgc    1620
gatctgcgcc agcccggagc cttcaccaac gctggtgcac tggaggggga ggcctgggcc    1680
```

```
ggggtgatcg atgccctcgg ccgcccggac cccgacggaa cctatgccgg cgccttgagc   1740
gctccggctt ccggcccccg ctccgaggac ggcggcggga gctga                  1785

<210> SEQ ID NO 3
<211> LENGTH: 1785
<212> TYPE: DNA
<213> ORGANISM: Artificial Sequence
<220> FEATURE:
<223> OTHER INFORMATION: codon optimized valine decarboxylase

<400> SEQUENCE: 3
atgagtacca gctctgccag ttccggtccg gacctgccgt ttggtccgga agatacgccg     60
tggcaaaaag ctttctcccg tctgcgtgcc gttgatggcg tcccgcgtgt gaccgccccg    120
tcatcggacc cgcgtgaagt ttacatggat attccggaaa tcccgtttag caaagtccag    180
attccgccgg acggtatgga tgaacagcaa tacgcagaag ctgaatctct gtttcgtcgc    240
tatgtggatg cccagacccg caacttcgca ggctatcaag ttacgagcga tctggactat    300
cagcatctgt ctcactacct gaatcgtcat ctgaacaatg ttggtgatcc gtatgaaagc    360
tctagttaca ccctgaacag caaagttctg aacgcgccg tcctggatta ttttgccagt     420
ctgtggaatg caaaatggcc gcacgacgca tccgatccgg aaacctattg ggctacgtg     480 ctgacgatgg ttcctcaga aggcaacctg tatggtctgt ggaatgcccg cgactacctg     540
agcggtaaac tgctgcgtcg ccaacatcgt gaagctggcg gtgataaagc gtcagtggtt    600
tatacccagg cactgcgtca tgaaggccaa tcgccgcacg cctacgaacc ggttgcattt    660
ttcagtcagg ataccccatta ttccctgacg aaagcggtcc gcgtgctggg cattgacacc   720
tttcactcta tcggttcgag ccgttatccg gatgaaaaacc cgctgggtcc gggcaccccg   780
tggccgacgg aagttccgag cgtcgatggc gctattgatg ttgacaaact ggcgtcactg    840 gtccgcttt tcgcctcgaa aggttatccg atcctggtta gcctgaatta cggctctacc     900
ttcaagggtg cgtatgatga tgtgccggcg gttgcacagg cagtccgtga tatttgcacg    960
gaatacggcc tggaccgtcg ccgtgtgtat catgatcgct ctaaagatag tgactttgat   1020
gaacgtagtg gtttctggat tcacattgat gccgcactgg gtgctggtta tgccccgtat   1080
ctgcaaatgg cccgcgacgc aggcatggtc gaagaagcac cgccggtgtt tgatttccgt   1140
ctgccggaag ttcattctct gaccatgagt ggccacaaat ggatgggtac gccgtgggcc   1200
tgtggtgtgt acatgacccg taccggtctg caaatgaccc cgccgaaatc tagtgaatat   1260
atcggtgcag ctgacaccac gtttgccggc agccgcaacg gtttctcctc actgctgctg   1320
tgggattatc tgtcccgtca ttcatacgat gacctggttc gcctggcggc cgactgtgat   1380
cgtctggctg gctatgcgca cgatcgcctg ctgaccctgc aagacaaact gggtatggat   1440
ctgtgggtgg cacgttcgcc gcaaagcctg acggttcgct ttcgtcagcc gtgcgctgac   1500
attgtccgta atactcgct gagctgtgaa accgtgtatg aagataacga acaacgcacg     1560
tatgtgcatc tgtacgcggt tccgcacctg acccgtgaac tggtcgacga actggttcgt   1620
gatctgcgtc agccgggtgc cttcaccaat gctggcgcgc tggaaggtga agcatgggca   1680
ggcgtgattg atgcgctggg tcgtccggac ccggatggca cctatgctgg tgcgctgtcc   1740
gcaccggcat caggtccgcg tagcgaagat ggcggtggca gctaa                  1785

<210> SEQ ID NO 4
<211> LENGTH: 51
<212> TYPE: DNA
```

```
<213> ORGANISM: Artificial Sequence
<220> FEATURE:
<223> OTHER INFORMATION: primer

<400> SEQUENCE: 4
agacagcata tgcatcatca ccatcaccac agtaccagct ctgccagttc c         51

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
agacaggaat tcttagctgc caccgccatc                                  30

<210> SEQ ID NO 6
<211> LENGTH: 37
<212> TYPE: DNA
<213> ORGANISM: Artificial Sequence
<220> FEATURE:
<223> OTHER INFORMATION: primer

<400> SEQUENCE: 6
agacaggaat tcatgtcaac ttcctccgct tcttccg                          37

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7
agacagggta cctcagctcc cgccgccgt                                   29

<210> SEQ ID NO 8
<211> LENGTH: 1119
<212> TYPE: DNA
<213> ORGANISM: Artificial Sequence
<220> FEATURE:
<223> OTHER INFORMATION: codon optimized alaD

<400> SEQUENCE: 8
atgaaaattg gtataccgaa ggaaattaaa aataatgaaa accgcgttgc cattacacct    60
gccggtgtga tgactttagt caaggccggg cacgacgtgt atgtcgaaac cgaagcaggg   120
gcgggcagcg gcttttccga ttcggaatat gaaaaagcag gagcagttat agttactaag   180
gccgaagacg cctgggcggc tgaaatggtt ttgaaagtaa aggagcccct ggcagaggaa   240
tttcggtact ttagaccggg acttatatta tttacctacc ttcatttagc ggcggccgag   300
gcgttgacga aggccctggt ggaacagaaa gttgtaggta tcgcctacga acggtccaa    360 ctggccaacg gaagccttcc gttattaacc cctatgtccg aagtggccgg gcggatgtcc   420
gtccaggtcg gagcacagtt tttagaaaag ccacacggtg ggaagggcat tttattggga   480 gggggttccgg gggtacggcg tggaaaagtt acgattattg ggggggggaac tgctggcact   540 aacgctgcca agatagcggt ggggttgggg gctgacgtca cgatacttga tataaacgcg   600
gaacgcctga gagagttaga cgatttgttc ggagatcaag ttaccacgtt gatgagcaat   660
tcatatcaca ttgcagaatg cgttagagaa agtgacctgg tagtgggtgc tgtgctgatc   720 cccgggggcaa aggccccaaa gttagtaacc gaggagatgg tccgtagcat gacgccaggt   780
```

| | |
|---|---|
| agtgtcttag tcgatgtcgc cattgaccag ggtggaatct tcgaaacaac cgaccgtgtc | 840 |
| acgacccatg acgaccccac ctatgtcaaa cacggtgtcg tacactatgc ggtcgcgaac | 900 |
| atgccaggag ctgtacctcg caccagcacg tttgcgctta ccaatgtgac catcccgtat | 960 |
| gccttgcaga tcgccaacaa gggataccgt gctgcctgtt tagataatcc agcgttgtta | 1020 |
| aagggtatca acaccttgga tggacatatc gtttacgagg ccgttgccgc agcacataat | 1080 |
| atgccatata ccgatgtcca ttctcttctg caaggatga | 1119 |

```
<210> SEQ ID NO 9
<211> LENGTH: 52
<212> TYPE: DNA
<213> ORGANISM: Artificial Sequence
<220> FEATURE:
<223> OTHER INFORMATION: primer

<400> SEQUENCE: 9
```

| | |
|---|---|
| agacagggta cctttcacac aggaaacaat gaaaattggt ataccgaagg aa | 52 |

```
<210> SEQ ID NO 10
<211> LENGTH: 51
<212> TYPE: DNA
<213> ORGANISM: Artificial Sequence
<220> FEATURE:
<223> OTHER INFORMATION: primer

<400> SEQUENCE: 10
```

| | |
|---|---|
| agacagctgc agtcatcctt gcagaagaga atggaagcga attttatcag c | 51 |

```
<210> SEQ ID NO 11
<211> LENGTH: 75
<212> TYPE: DNA
<213> ORGANISM: Artificial Sequence
<220> FEATURE:
<223> OTHER INFORMATION: primer

<400> SEQUENCE: 11
```

| | |
|---|---|
| gctcgtataa tgtgtggaat tgtgagcgga taacaatttc acacaggaaa caatgagcca | 60 |
| gcaagtcatt atttt | 75 |

```
<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
```

| | |
|---|---|
| ttaattcata aacgcaggtt gttt | 24 |

```
<210> SEQ ID NO 13
<211> LENGTH: 57
<212> TYPE: DNA
<213> ORGANISM: Artificial Sequence
<220> FEATURE:
<223> OTHER INFORMATION: primer

<400> SEQUENCE: 13
```

| | |
|---|---|
| agacagctgc aggctgttga caattaatca tcggctcgta taatgtgtgg aattgtg | 57 |

```
<210> SEQ ID NO 14
<211> LENGTH: 53
<212> TYPE: DNA
```

```
<213> ORGANISM: Artificial Sequence
<220> FEATURE:
<223> OTHER INFORMATION: primer

<400> SEQUENCE: 14
agacagctgc agttaattca taaacgcagg ttgttttgtc cgagccggaa gag         53
```